United States Patent
Thyagarajan

(10) Patent No.: US 10,709,889 B2
(45) Date of Patent: Jul. 14, 2020

(54) LOCALIZED ELECTROMAGNETIC FIELD CONTROL IN IMPLANTABLE BIOMEDICAL PROBES USING SMART POLYMERS

(71) Applicant: Palo Alto Research Center Incorporated, Palo Alto, CA (US)

(72) Inventor: Krishnan Thyagarajan, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 185 days.

(21) Appl. No.: 15/908,211

(22) Filed: Feb. 28, 2018

(65) Prior Publication Data
US 2019/0262614 A1    Aug. 29, 2019

(51) Int. Cl.
| *A61N 1/36* | (2006.01) |
| *A61N 1/05* | (2006.01) |
| *A61N 1/372* | (2006.01) |
| *A61N 2/02* | (2006.01) |
| *A61N 1/08* | (2006.01) |

(52) U.S. Cl.
CPC .......... *A61N 1/36128* (2013.01); *A61N 1/05* (2013.01); *A61N 1/36* (2013.01); *A61N 1/37223* (2013.01); *A61N 2/02* (2013.01); *A61N 1/0534* (2013.01); *A61N 1/08* (2013.01); *A61N 1/3606* (2013.01); *A61N 1/36067* (2013.01); *A61N 1/36132* (2013.01); *A61N 1/36157* (2013.01); *A61N 1/36171* (2013.01)

(58) Field of Classification Search
CPC ........ A61N 1/36128; A61N 1/36; A61N 1/05; A61N 2/02; A61N 1/37223; A61N 1/0534; A61N 1/36132; A61N 1/36067; A61N 1/36157; A61N 1/36171; A61N 1/3606; A61N 1/08

See application file for complete search history.

(56) References Cited

U.S. PATENT DOCUMENTS

| 8,554,329 B1 * | 10/2013 | Mann .................. H04R 25/606 607/56 |
| 2007/0073130 A1 | 3/2007 | Finch et al. |
| 2010/0030045 A1 * | 2/2010 | Gottlieb ............. A61B 5/14532 600/347 |
| 2011/0152725 A1 * | 6/2011 | Demir ................. A61B 5/0031 600/587 |

(Continued)

OTHER PUBLICATIONS

J. M. Harberl et al., Light-Controlled Actuation, Transduction, and Modulation of Magnetic Strength in Polymer Nanocomposites, Advanced Functional Materials 24, (2014), pp. 3179-3186.*

(Continued)

*Primary Examiner* — Catherine M Voorhees
(74) *Attorney, Agent, or Firm* — Shun Yao; Park, Vaughan, Fleming & Dowler LLP

(57) ABSTRACT

One embodiment provides an implantable biomedical probe. The probe can include a substrate and one or more metallic coils positioned above the substrate. A respective metallic coil is configured to generate an electromagnetic field in response to an alternating current flowing through the metallic coil. The probe can further include a smart polymer layer positioned above the metallic coils. The smart polymer layer can include at least one photo-switching magnetic material that changes magnetic susceptibility in response to optical stimuli.

20 Claims, 13 Drawing Sheets

(56) References Cited

U.S. PATENT DOCUMENTS

2016/0215253 A1* 7/2016 Bhola .................... C12M 41/48
2017/0276562 A1* 9/2017 Shimada ................. C23C 14/34
2019/0020291 A1* 1/2019 Cappelleri ............. H02N 10/00

OTHER PUBLICATIONS

T. Ware, D. Simon, R. L. Rennaker II, and W. Voit, Smart Polymers for Neural Interfaces, Polymer Reviews, vol. 53, 2013—Issue 1 (2012).

J. M. Haberl, A. Sanchez-Ferrer, A. M. Mihut, H. Dietsch, A. M. Hirt and R. Mezzenga, Light-Controlled Actuation, Transduction, and Modulation of Magnetic Strength in Polymer Nanocomposites, Adv. Func. Mater. 24, 3179-3186 (2014).

S.-I. Ohkoshi and H. Tokoro, Photomagnetism in Cyano-Bridged Bimetal Assemblies, Acc. Chem. Res. 45 (10), 1749-1758 (2012).

S.-I. Ohkoshi and K. Hashimoto, New Magnetic Functionalities Presented by Prussian Blue Analogues, Elec. Chem. Soc. Interface, 34-38 (2002).

J. S. Bellinger, C. Piamonteze, R. V. Chopdekar, M. Lilberati, E. Arenholz and Y. Suzuki, Room-Temperature Photomagnetism in the Spinel Ferrite (Mn, Zn, Fe)3O4 as Seen via Soft X-Ray Magnetic Circular Dichroism, Phys. Rev. B 80, 140413 (2009).

T. Yamamoto, E. A. Yurieva, K. Tsuda, T. Hosomi, S. M. Aldoshin and Y. Einaga, Gigantic Photomagnetic Effect at Room Temperature in Spiropyran-Pritected FePt Nanoparticles, Phys. Status Solidi RRL, 1700161 (2017).

* cited by examiner

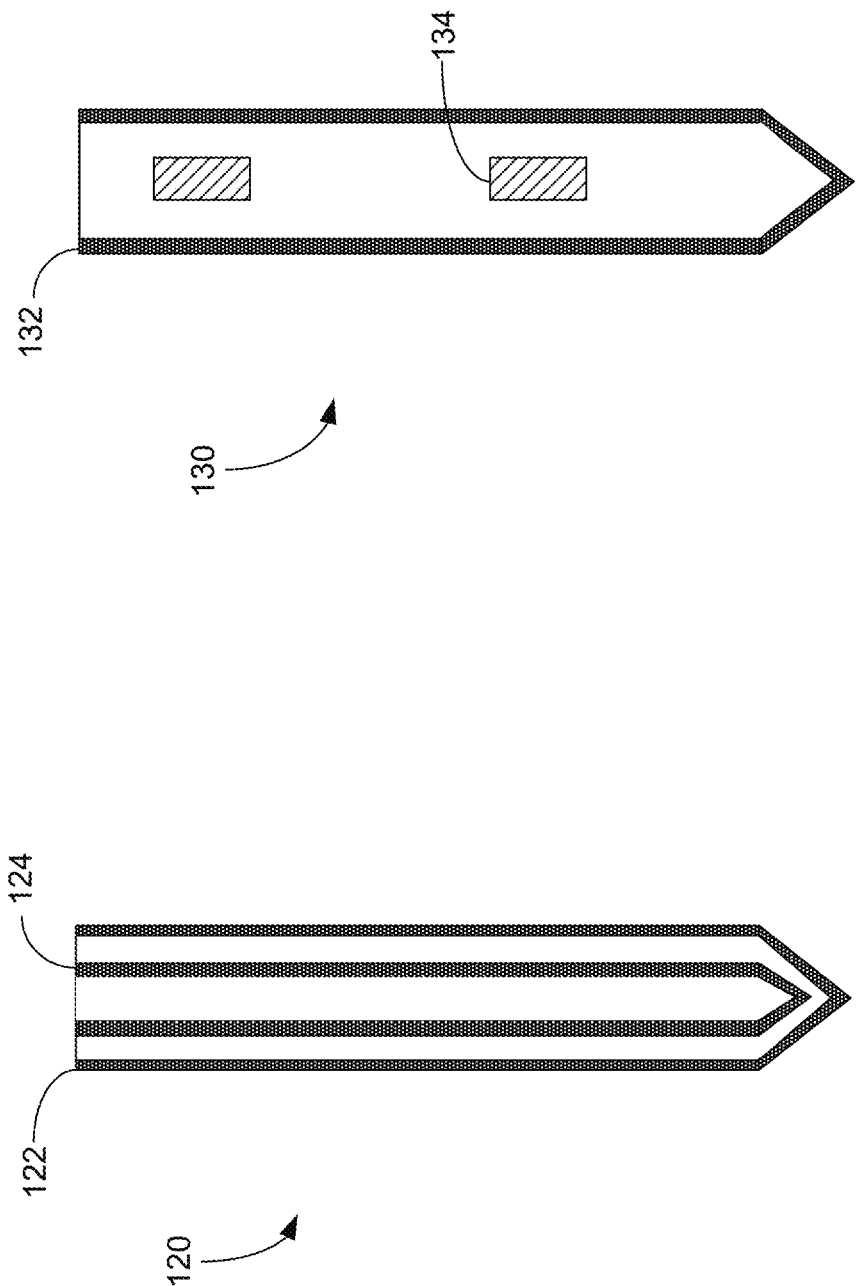

5A

5B

5C

5D

5E

5F

5G

5H

5I

5J

5K

LOCALIZED ELECTROMAGNETIC FIELD CONTROL IN IMPLANTABLE BIOMEDICAL PROBES USING SMART POLYMERS

STATEMENT OF GOVERNMENT-FUNDED RESEARCH

This invention was made with U.S. government support under Grant No. NIH 1U01NS099700-01, entitled "Development of a Novel Focused Magnetic Stimulation Technology with Minimally Invasive Approach for Vagus Nerve Modulation and Regulation of Anti-inflammatory Pathway," awarded by the National Institute of Health (NIH). The U.S. government has certain rights in this invention.

BACKGROUND

Field

This disclosure is generally related to implantable biomedical probes. More specifically, this disclosure is related to implantable biomedical probes that allow for localized electromagnetic field control.

Related Art

Implantable biomedical devices and systems have been developed in recent years to treat a variety of ailments, including neurological disorders, psychological disorders, hearing or visual impairments, etc. For example, cochlear implants have been used to restore hearing to the deaf, and retinal visual prostheses have been used to restore vision to the blind. A surgical procedure is often required to implant the biomedical device or system into a patient's body.

Many implantable devices achieve their treatment functions by creating electromagnetic fields that can stimulate or suppress biological matter locally. In general, these implantable devices can be more effective when targeting very specific small volumes in the body and/or nerve bundles. This can be achieved by inserting the device close to the targeted region in order to achieve effective treatment results. For example, electrodes can be implanted into a patient's brain to deliver electrical pulses to the brain in order to alleviate symptoms of Parkinson's disease.

Conventional implantable biomedical devices, such as implantable probes, typically have a local electromagnetic field profile that is predetermined at the time of design and fabrication. This means that they cannot react to changes in a patient's body. Furthermore, the invasive nature of the implantation process makes it difficult to replace a device that has been implanted.

SUMMARY

One embodiment can provide an implantable biomedical probe. The probe can include a substrate and one or more metallic coils positioned above the substrate. A respective metallic coil is configured to generate an electromagnetic field in response to an alternating current flowing through the metallic coil. The probe can further include a smart polymer layer positioned above the metallic coils. The smart polymer layer can include at least one photo-switching magnetic material that changes magnetic susceptibility in response to optical stimuli.

In a variation on this embodiment, the substrate can include Si, and the substrate's thickness can be between 100 and 300 nm.

In a variation on this embodiment, the metallic coils can be coplanar, and a metallic coil can be positioned around edges of the substrate.

In a variation on this embodiment, the probe can further include a first insulation layer positioned between the substrate and the metallic coils.

In a further variation, the first insulation layer comprises $SiO_2$.

In a further variation, a thickness of the first insulation layer is between 100 and 200 nm.

In a variation on this embodiment, the probe can further include a second insulation layer positioned above the metallic coils.

In a further variation, the second insulation layer can include $SiNO_x$.

In a further variation, the second insulation layer can have a thickness between 100 nm and 1 micron.

In a further variation, the smart polymer layer can be positioned between the metal coils and the second insulation layer.

In a further variation, the smart polymer layer is positioned above the second insulation layer.

In a variation on this embodiment, the respective metallic coil comprises an Au layer.

In a further variation, the Au layer can have a thickness between 1 and 10 microns and a width between 5 and 30 microns.

In a further variation, the respective metallic coil can further include a Ti—W layer positioned above the Au layer and a Mo—Cr layer positioned between the substrate and the Au layer. The Ti—W layer can have a thickness between 1 and 10 nm, and the Mo—Cr layer can have a thickness between 10 and 50 nm.

In a variation on this embodiment, the smart polymer layer can include one or more of: liquid crystal polymers with anisotropic $Fe2O3$ nanofillers, $Cu2[Mo(CN)8].8H2O$ (CuMo), $RbMn[Fe(CN)6]$ (RbMnFe), $Co3[W(CN)8]2.(pyrimidine)4.6H2O$ (CoW), $Fe2[Nb(CN)8].(4-pyridinealdoxime)8.2H2O$ (FeNb), liquid crystal polymers embedded with spinel ferrites $(Mn, Zn, Fe)3O4$, and liquid crystal polymers embedded with Spiropyran-protected FePt nanoparticles.

One embodiment can provide a biomedical system. The system can include an implantable probe, which can include a substrate, one or more metallic coils positioned above the substrate, and a smart polymer layer positioned above the metallic coils. A respective metallic coil is configured to generate an electromagnetic field in response to an alternating current flowing through the metallic coil. The smart polymer layer can include at least one photo-switching magnetic material that changes magnetic susceptibility in response to light. The system can further include a probe connector electrically coupled to the implantable probe and a printed circuit board. The probe connector can include a plurality of metallic fingers. The printed circuit board can include a cable connector and an input/output port electrically coupled to each other. The cable connector can be electrically coupled to metallic fingers of the probe connector via a flexible cable, and the input/output port can be electrically coupled to an external power-and-control unit.

BRIEF DESCRIPTION OF THE FIGURES

FIG. 1B shows an exemplary biomedical probe with multiple loops of coil, according to one embodiment.

FIG. 1C shows an exemplary biomedical probe with sensors, according to one embodiment.

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Overview

The embodiments described herein solve the technical problem of enabling dynamic control of electromagnetic fields generated by implantable biomedical probes. More specifically, the biomedical probes can incorporate biocompatible smart polymers, whose magnetic susceptibility can change responsive to external stimuli (e.g., light). In some embodiments, the biomedical probes can include metallic coils fabricated on a Si substrate. Moreover, a layer of smart polymer (e.g., polymer embedded with ferromagnetic nanoparticles, spinel ferrites, Spiropyran-protected FePt nanoparticles) can be deposited over the metallic coils. Light applied externally, penetrating the body tissue, can change the magnetic susceptibility of the smart polymer, thus the local magnetic susceptibility. Consequently, the excited electromagnet field profile around the probe can be changed by shining light at different locations of the probe.

Implantable Probe

Implantable electromagnetic probes are one type of implantable biomedical device that can excite electromagnetic fields within biological matter (e.g., the brain) in order to modify the property of or stimulate the biological matter. More specifically, an electromagnetic probe can include a metallic coil, which can generate an electromagnetic field when an alternating current flows through the coil. It has been shown that an electrical field induced in the brain can influence brain activity.

Figure 1A:
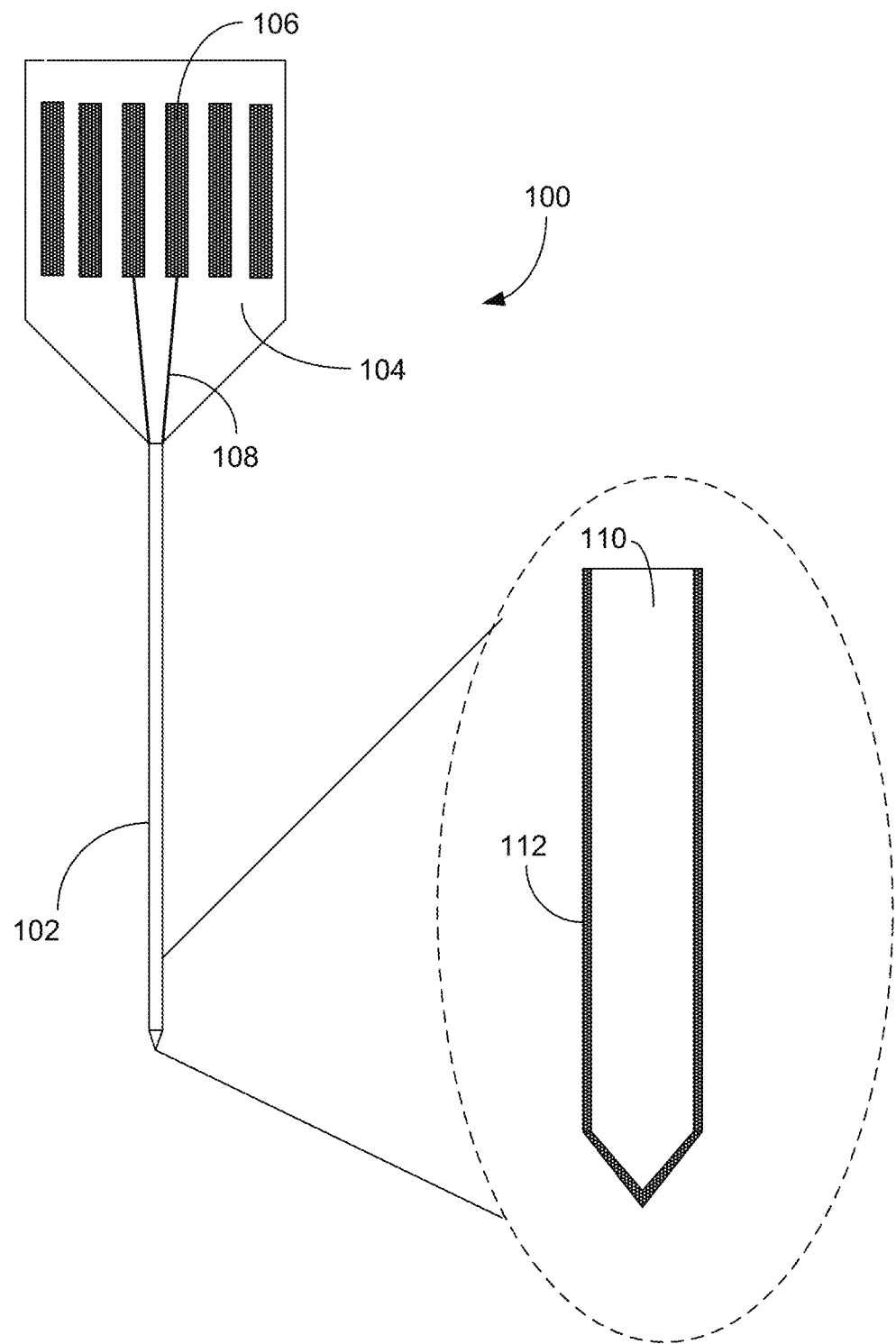
FIG. 1A shows an exemplary implantable biomedical probe, according to one embodiment.

FIG. 1A shows an exemplary implantable probe, according to one embodiment. Implantable probe 100 can include a probe body 102 and a connector 104. When in operation, probe body 100 can be implanted into a human's body, such as the brain, and connector 104 can remain external to the body to facilitate coupling between probe body 102 and external circuit components. In some embodiments, connector 104 can include a number of metallic fingers (e.g., finger 106) for coupling with external circuit components and metal traces (e.g., metal trace 108) for coupling with metallic coil or coils on probe body 102.

Due to its invasive nature, the size (especially the cross-section) of probe body 102 needs to be kept small. In some embodiments, the cross-section of probe body 102 can be a few hundred microns by a few hundred microns. In one embodiment, the thickness of probe body 102 can be around 250 microns, and the width of probe body 102 can be around 100 to 150 microns. The length of probe body 102 can be chosen based on application or desired depth of penetration. In some embodiments, probe body 102 can be a few millimeters (e.g., 7 mm) long. On the other hand, the size of connector 104 needs to be adequately large to allow for easy handling by the surgeon. In some embodiments, the dimensions of connector 104 can be a few millimeters by a few millimeters, for example, 3 mm by 5 mm. In some embodiments, probe body 102 and connector 104 can be fabricated on the same substrate. Alternatively, they may be fabricated separately and bonded together using various wafer-bonding techniques.

FIG. 1A also shows the amplified view of a portion of probe body 102. As shown in the dashed circle, the probe body can include a substrate region 110 and a coil region 112. In some embodiments, substrate region 110 can include the part of the probe body that is not covered by metal, and coil region 112 can include the part of the probe body that is covered by metallic or conductive material, forming a coil-like structure. The coil can be a coplanar coil. In the example shown in FIG. 1A, coil region 112 can include a metal strip covering the edges of the top surface of probe body 102, forming a single-loop coil. Such a metal strip can be formed by depositing a metal layer around the edges of probe body 102. Note that coil region (or metal strip) 112 can be coupled to metal traces (e.g., metal trace 108) located on connector 104, thus facilitating current injection into coil region 112. For example, either end of the single loop coil can be coupled to a metal trace on connector 104, and the two metal traces can be coupled to the two outputs of an AC current source, thus resulting in AC current flowing through the single loop coil, generating an electromagnetic (EM) field in regions surrounding probe body 102.

In some embodiments, the width of metal strip 112 can be between 1 and 30 microns, preferably around 10 microns; and the thickness of metal strip 112 can be between 1 and 30 microns, preferably between 1 and 10 microns (e.g., 2 microns). Metal strip 112 typically can include gold due to its biocompatibility, corrosion resistance, and anti-inflammatory properties. In some embodiments, the gold strip can also be coated with other types of metallic materials, such as Molybdenum-Chromium (Mo—Cr) alloy and Titanium-Tungsten (Ti—W) alloy, to provide better biocompatibility and greater strength.

To enable post-implantation modulation of the EM field distribution around the implanted probe, in some embodiments, coil region (or metal strip) 112 can be completely or partially coated with a layer of biocompatible smart polymer, which can respond to light excitation. More specifically, the smart polymer can include at least one photo-switching magnetic material, whose magnetic properties can be controlled by optical stimuli. Examples of smart polymers can include, but are not limited to: liquid crystal polymers with anisotropic $Fe_2O_3$ nanofillers, $Cu_2[Mo(CN)_8] \cdot 8H_2O(CuMo)$, $RbMn[Fe(CN)_6]$ (RbMnFe), $Co_3[W(CN)_8]_2 \cdot (pyrimidine)_4 \cdot 6H_2O$ (CoW), $Fe_2[Nb(CN)_8] \cdot (4\text{-pyri-dinealdoxime})_8 \cdot 2H_2O$ (FeNb), and liquid crystal polymers embedded with spinel ferrites (Mn, Zn, Fe)$_3O_4$ or Spiropyran-protected FePt nanoparticles. Due to its photomagnetic property, the magnetic susceptibility of the smart polymer can be changed locally by shining light at specific locations. Under appropriate conditions, the permeability of the probe can be changed by up to 40%. As a result, one can modulate the EM field excited by current flowing through coil region 112 by shining light at specific locations.

In addition to the single-loop structure shown in FIG. 1A, other types of coils (e.g., multi-loop concentric coils or metal strips having different geometries) can also be formed on the probe body. As long as an EM field can be excited, the invention is not limited by the exact geometry of the coil. FIG. 1B shows a biomedical probe with multiple loops of coils, according to one embodiment. In FIG. 1B, probe 120 can include at least two concentric loops, loop 122 and loop 124. AC current flowing through these loops can create an EM field around probe 120. It is also possible to have more loops or a metal layer with different geometries.

Other than metal coils/strips for exciting the EM field, in some embodiments, the implantable probe can also include a number of sensors that can measure the electrical/magnetic signals generated by the neurons, thus providing feedback to the control of the probe. FIG. 1C shows a biomedical probe with sensors, according to one embodiment. Implantable probe 130 not only includes a metal strip/coil 132, but also includes a number of sensors, such as sensor 134. These sensors can be located in the substrate region (i.e., the region not covered by metal coil 132) of implantable probe 130. In such a scenario, the sensors and coil may be turned on in an alternating way. Alternatively, these sensors can be located on the back surface of implantable probe 130, and the sensors and coil can be turned on simultaneously. For simplicity of illustration, electrical connections between the sensors and the probe connector are not shown in the drawing. Such connections can typically be achieved via metal traces.

Figure 2A:
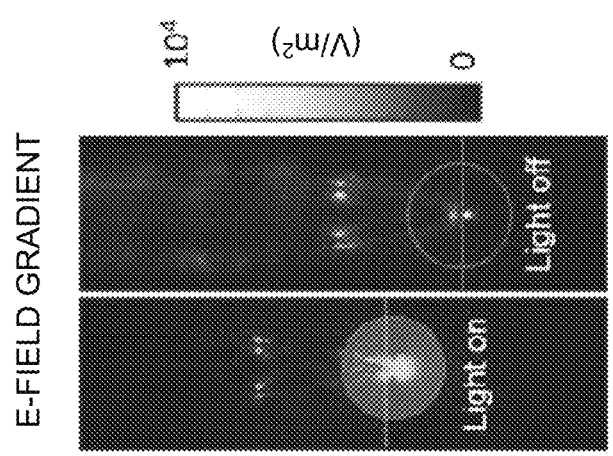
FIG. 2A illustrates a simulated distribution of an electrical field gradient around an implantable probe with and without light, according to one embodiment.
Figure 2A:

FIG. 2A illustrates a simulated distribution of an electrical field gradient around an implantable probe with and without light, according to one embodiment. In FIG. 2A, implantable probe 202 can be similar to implantable probe 100 shown in FIG. 1, and can include a single-loop coil. The electric field (E-field) gradients at regions surrounding the probe can be color-coded. The far right drawing shows a scenario where no light shines onto the probe. As one can see, the probe tip shows a stronger E-field gradient (indicated by yellow). The middle drawing shows a scenario where light shines onto a particular location on the probe. As one can see, the E-field gradient has become significantly enhanced at the location where light shines (indicated by the circle).

Figure 2B:
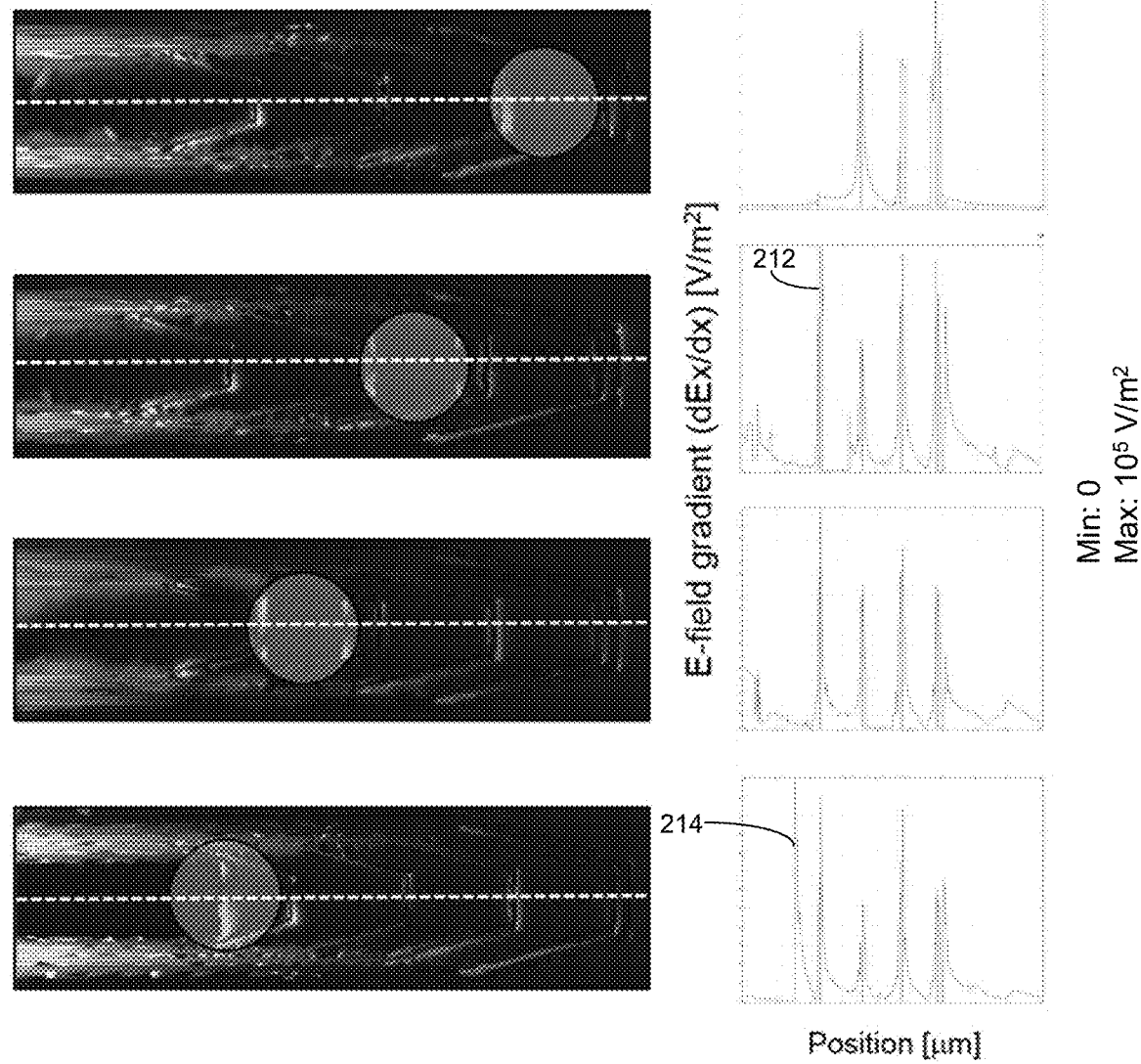
FIG. 2B illustrates a simulated distribution of an electrical field gradient around an implantable probe when light shines on different portions of the probe, according to one embodiment.

Increasing the number of loops in the coil can increase the intensity of the EM field. Moreover, when light shines on different loops, it can excite E-field gradients at different locations. FIG. 2B illustrates a simulated distribution of an electrical field gradient around an implantable probe when light shines on different portions of the probe, according to one embodiment. In the example, shown in FIG. 2B, the probe can include a number of concentric coplanar coils coated with smart polymer, similar to the one shown in FIG. 1B, but with more loops than shown in FIG. 1B.

More specifically, the left-side drawings show the simulated E-field gradients around the probe, with the E-field gradients color-coded. The circles indicate the positions of photomagnetic activity, i.e., where local magnetic susceptibility changes due to light. In some embodiments, a finite-element method (FEM) is used to simulate the EM field. As one can see from the drawings, as light moves from the right side (or the end) of the probe along its longitudinal axis, the excited E-field tends to move with the light. In other words, a local change in magnetic susceptibility results in changes in the excited E-field.

The right-side drawings of FIG. 2B plot the simulated E-field gradient along the longitudinal axis of the probe as a function of the position of the light. The longitudinal axis of the probe is indicated by the dashed line in each drawing. As one can see from FIG. 2B, the peaks of the E-field gradient shift with the light (as indicated by peaks 212 and 214). In other words, the discontinuity of the magnetic susceptibility can cause the peaks of the E-field gradient to shift positions. This makes it possible to modulate the local EM field profile by modulating the local magnetic susceptibility. In addition to photomagnetic effect, other properties of the smart polymer, such as piezoelectricity and shape memory, may also be used to modulate the local electrical field.

Figure 3A:
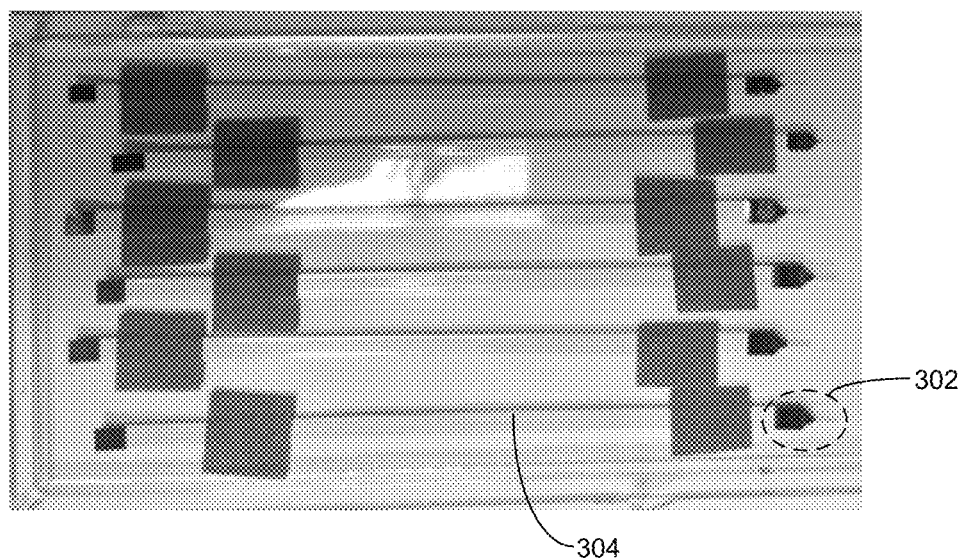
FIG. 3A shows a photo of a number of fabricated implantable probes, according to one embodiment.

In order for the implantable probes to function when implanted in a human's body (e.g., within the human brain), the implantable probes may need to couple to external power and control circuitries. Specially designed connectors, cables, and printed circuit boards (PCBs) can be used to facilitate the coupling between the implanted probe and the external power and control circuit components. FIG. 3A shows a photo of a number of fabricated implantable probes, according to one embodiment. Each implantable probe (e.g., probe 302) can be attached, via its connector, to a cable. For example, probe 302 is attached to cable 304. In some embodiments, a cable can include multiple wires bundled together, and the connector of a probe can be attached to one end of the cable using a wire-bonding technique. The cable can be made of a flexible material. In some embodiments, each flexible cable can include a socket-type connector (e.g., a zero-insertion-force (ZIF) connector) for coupling to an external plug-and-play (PnP) board, which can enable plug-and-play of the implantable probe. For example, the PnP board can include a ZIF socket that can receive the pre-stripped bare end of the flexible cable.

Figure 3B:
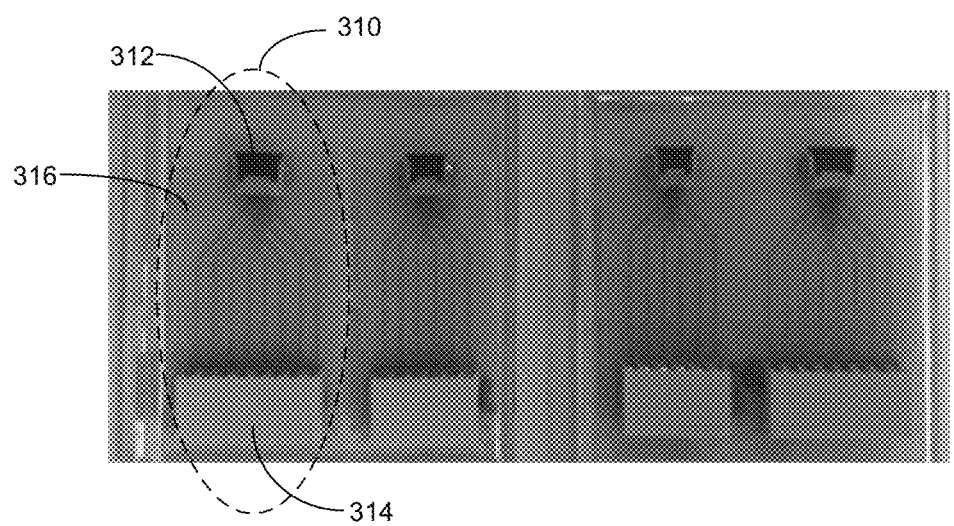
FIG. 3B shows a photo of a number of plug-and-play boards, according to one embodiment.

FIG. 3B shows a photo of a number of plug-and-play boards, according to one embodiment. Each PnP board (e.g., PnP board 310) can include a cable-connector 312, an input/output (I/O) port 314, and a printed circuit board (PCB) 316. Cable-connector 312 can match the connector on the flexible cable, thus facilitating coupling between the flexible cable and the PnP board. In some embodiments, cable-connector 312 can include a ZIF socket. I/O port 314 can facilitate coupling between PnP board 310 and external control and power circuitry. Depending on the applications or the configuration of the probe connector, printed circuit board 316 can include metal traces of different patterns. For example, a probe connector may include six metal fingers (e.g., as shown in FIG. 1A), meaning that up to six connections can be made to the probe. Accordingly, the cable connector may only have six lead wires, and the I/O port can have six pins. In some embodiments, the I/O port on the PnP board can comply with an industry standard, to allow for an easy interface between the PnP board and the external power and control circuit components.

Figure 4:
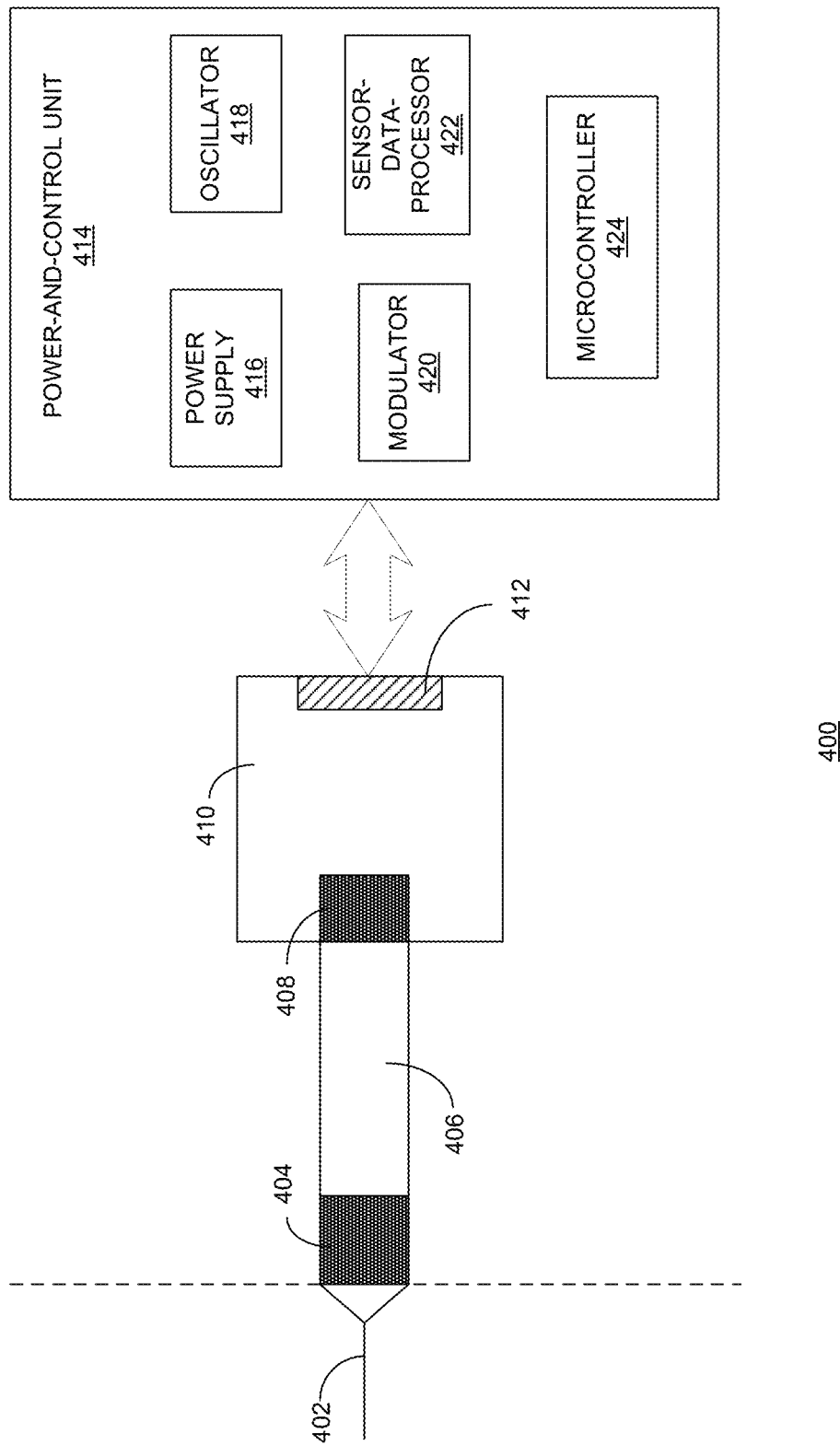
FIG. 4 illustrates an exemplary biomedical system with an implantable electromagnetic probe, according to one embodiment.

FIG. 4 illustrates an exemplary biomedical system with an implantable electromagnetic probe, according to one embodiment. Biomedical system 400 can include an implantable probe 402, a probe connector 404, a flexible cable 406, a cable connector 408, a PCB 410, an I/O port 412, and a power-and-control unit 414. More specifically, power-and-control unit 414 can include a power supply 416, an oscillator 418, a modulator 420, a sensor-data-processor 422, and a microcontroller 424.

Implantable probe 402 can be imbedded into biological matter (e.g., a human brain), whereas other components remain external to the biological matter, as indicated by the dashed line. Implantable probe 402 can be coupled to one end of flexible cable 406 via probe connector 404, which can be fabricated on the same substrate as implantable probe 402. The other end of flexible cable 406 can be coupled to (e.g., inserted into) cable connector 408, which can be a ZIF socket that receives the pre-stripped end of flexible cable 406. Both cable connector 408 and I/O port 412 can be located on PCB 410, and metal traces on PCB 410 can couple cable connector 408 and I/O port 412. I/O port 412 can interface with power-and-control unit 414, thus facilitating coupling between implantable probe 402 and various components of power-and-control unit 414.

More specifically, power supply 416 can provide power (e.g., current) to implantable probe 402. Oscillator 418 and modulator 420 together modulate the output current. In some embodiments, power supply 416 can provide an alternating current to probe 402. The intensity of the current can be between 1 and 60 mA, preferably between 5 and 30 mA. In one embodiment, the current intensity can be around 10 mA. In some embodiments, the frequency of the alternating current can be between 1 and 5 kHz, preferably between 2 and 4 kHz. In one embodiment, the frequency can be around 3 kHz. Sensor-data-processor 422 can process data received from one or more sensors located on implantable probe 402. Microcontroller 424 can be responsible for controlling operations of various components within power-and-control unit 414. For example, microcontroller 424 can adjust the current intensity and frequency by adjusting the settings of power supply 416 and oscillator 418. In some embodiments, such adjustments can be made based on outputs from sensor-data-processor 422. In other words, microcontroller 424 can dynamically adjust operations of implantable probe 402 based on sensor data.

Note that in the example shown in FIG. 4, circuitries that provide power and control to the implantable probe are located external to the biological matter. In practice, it is also possible to reduce the size of these circuitries and implant them inside the biological matter along with the probe.

Fabricating Implantable Probes

Figure 5:
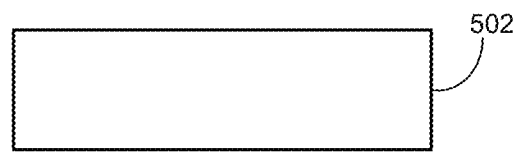
FIG. 5 illustrates an exemplary process for fabricating an implantable biomedical probe, according to one embodiment.
Figure 5:
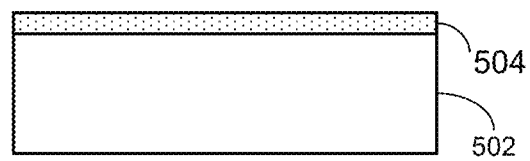
Figure 5:
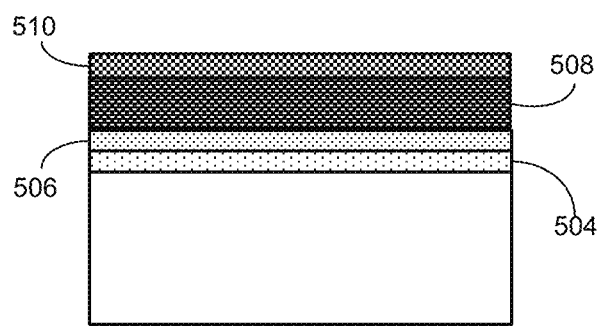
Figure 5:
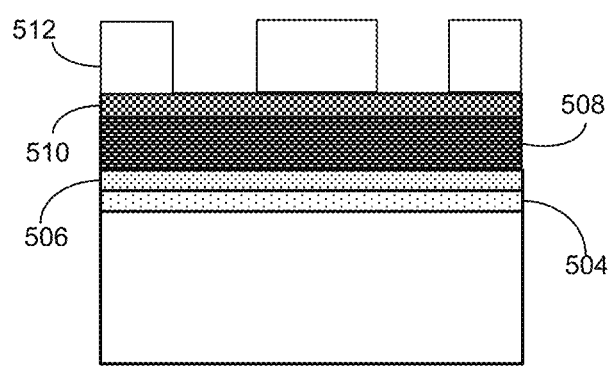
Figure 5:
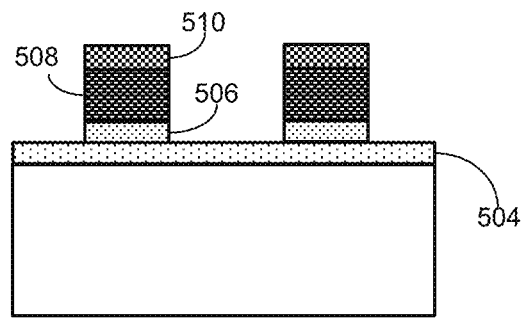
Figure 5:
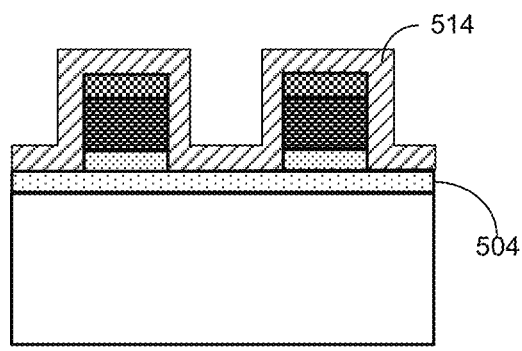
Figure 5:
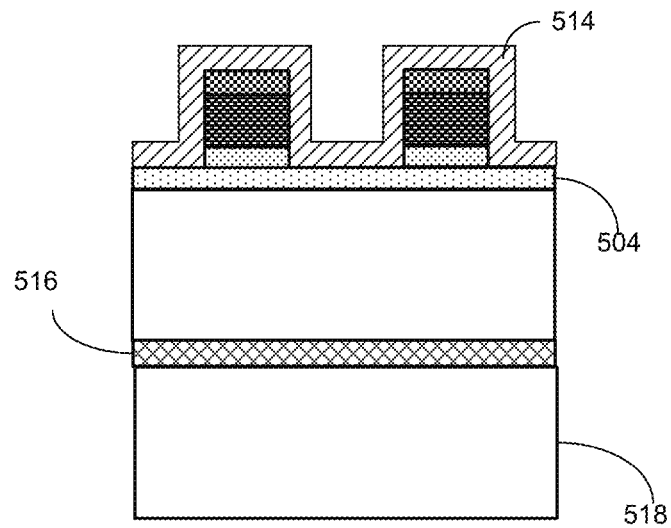
Figure 5:
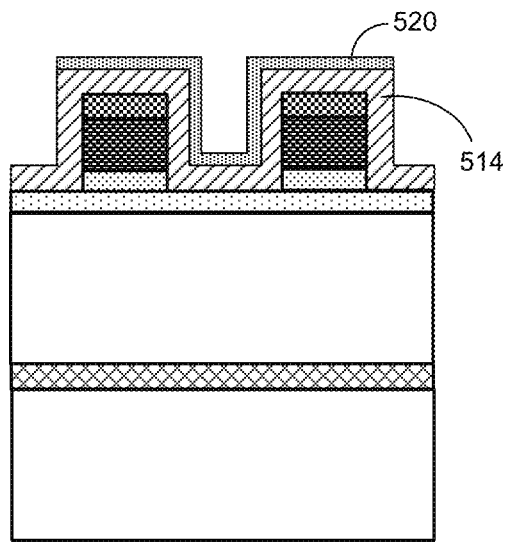
Figure 5:
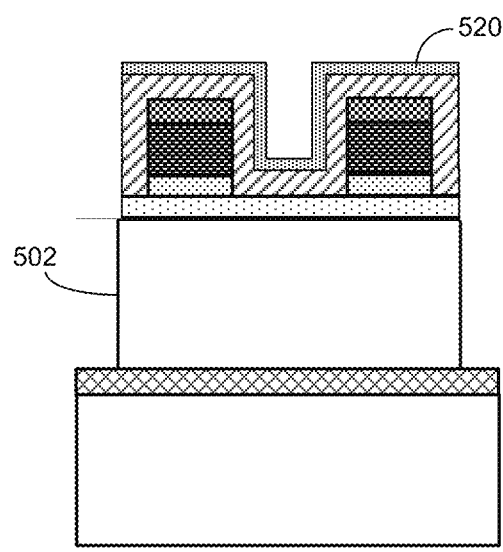
Figure 5:
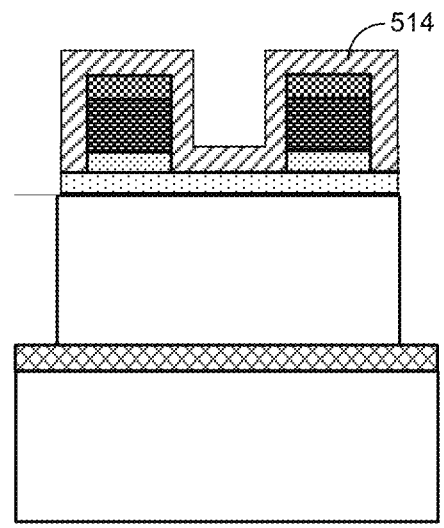
Figure 5:
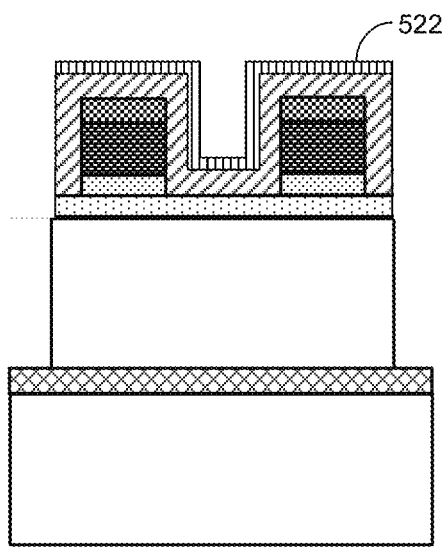
Figure 5:
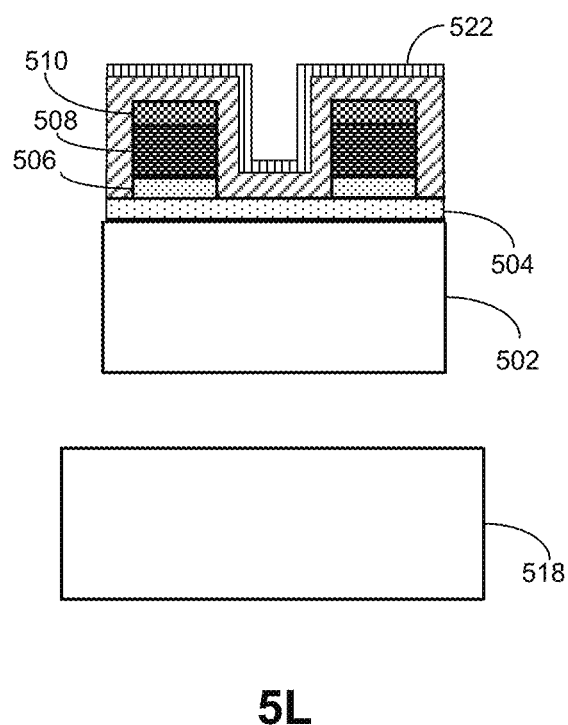

FIG. 5 illustrates an exemplary process for fabricating an implantable biomedical probe, according to one embodiment. In operation 5A, a substrate 502 is prepared. Substrate 502 can include a crystalline Si wafer having a diameter of around 50 mm (or 2 inches) and a thickness of around 250 microns. In addition to a crystalline Si wafer, other types of substrate can also be used, such as a polycrystalline silicon wafer. In some embodiments, preparing Si substrate 502 can include cleaning the wafer surface using oxygen plasma. In operation 5B, a thin layer of dielectric material (dielectric layer 504) can be deposited onto the surface of Si substrate 502 in order to provide insulation at the bottom of the probe. In some embodiments, dielectric layer 504 can include a layer of $SiO_2$, and the thickness of dielectric layer 504 can be between 100 and 200 nm, preferably around 150 nm. In some embodiments, depositing dielectric layer 504 can involve a chemical vapor deposition (CVD) process, such as plasma-enhanced CVD (PECVD). In a further embodiment, the PECVD operation can be performed at a temperature between 150 and 250° C.

In operation 5C, one or more metal layers can be deposited on dielectric layer 504. In some embodiments, a layer of Mo—Cr alloy (layer 506), a layer of gold (Au) (layer 508), and a layer of Ti—W alloy (layer 510) can be sequentially deposited on the surface of dielectric layer 504. In further embodiments, Mo—Cr layer 506 can have a thickness of between 10 and 50 nm (e.g., 20 nm), Ti—W layer 510 can have a thickness of between 1 and 10 nm (e.g., 3 nm), and gold layer 508 can have a thickness of between 1 and 30 microns, preferably between 1 and 10 microns (e.g., 2 microns). Note that, although a thicker gold layer can create a stronger E-field, one may need to consider the material cost and aspect ratio when fabricating the implantable probes.

In operation 5D, a patterned photoresist layer 512 can be deposited onto the top surface of metal layer 510. Forming patterned photoresist layer 512 can involve a photolithography technique, such as spinning, baking, exposure, and development of photoresist. In some embodiments, the mask can define metal regions on the probe, including the coil region in the probe body and the metal trace and finger regions in the probe connector.

In operation 5E, using the patterned photoresist layer as an etching mask, the one or more metal layers can be etched accordingly, forming the desired metal pattern that includes the coil (or coils), metal traces, and metal fingers. In some embodiments, different etching techniques can be used for etching the different metal layers. For example, Mo—Cr layer 506 and Au layer 508 can be wet-etched, whereas Ti—W layer 510 can be dry-etched. In one embodiment Mo—Cr layer 506 can be etched using a chrome etchant, such as CR44 manufactured by KMG Electronic Chemicals of Fort Worth, Tex.; and Au layer 508 can be etched with a gold etchant, such as TFA manufactured by Transene Company, Inc., of Danvers, Mass. In one embodiment, Ti—W layer 510 can be etched using a plasma-etching technique, such as inductively coupled plasma (ICP) etching. In some embodiments, the patterned metallic coil can have a width between 1 and 30 microns, preferably between 3 and 30 microns (e.g., 10 microns).

In operation 5F, a biocompatible insulation layer 514 can be deposited on the top surface of the entire structure, covering exposed surfaces of dielectric layer 504 and metal layers 506, 508, and 510. Biocompatible insulation layer 514 can have superior biocompatibility, capable of protecting the biological matter from any possible negative impact caused by the probe. Moreover, in some embodiments, biocompatible insulation layer 514 can include silicon oxynitride ($SiON_x$), and the thickness of biocompatible insulation layer 514 can be between 100 nm and 1 micron, preferably around 500 nm. In further embodiments, a PECVD process can be used to deposit $SiON_x$ layer 514. The PECVD process can be performed at a temperature between 100 and 200° C., preferably at around 150° C.

In operation 5G, the entire structure can be mounted, using a wax layer 516, onto a handling Si wafer 518. Handling Si wafer 518 facilitates easy handling of the wafer for later processes. In operation 5H, a patterned hard-mask layer 520 is formed on top of the structure to facilitate a subsequent deep reactive-ion etching (DRIE) operation. In some embodiments, hard-mask layer 520 can include an Al layer of around 200 nm and a Ti—W layer of around 50 nm. Patterned hard-mask layer 520 defines the boundary of each implantable probe. Windows within patterned hard-mask layer 520 correspond to locations of trenches that separate adjacent probe structures. Forming patterned hard-mask layer 520 can include a photolithography process followed by a metal-liftoff process. Alternatively, forming patterned hard-mask layer 520 can involve defining a via-mask and patterned hard-mask layer 520 using a dry-etching technique.

In operation 5I, a DRIE operation can be performed to etch Si substrate 502 using hard-mask layer 520 as an etching mask. In some embodiments, an ICP machine can be used to perform the DRIE operation. In operation 5J, hard-mask layer 520 can be removed. In some embodiments, a dry-etching process (e.g., ICP etching) can be used to remove hard-mask layer 520. In operation 5K, smart polymer layer 522 can be deposited on top of the probe structure. In some embodiments, a spin-coating technique can be used to deposit smart polymer layer 522. Smart polymer layer 522 can include at least one photo-switching magnetic material. Examples of smart polymers can include, but are not limited to: liquid crystal polymers with anisotropic $Fe_2O_3$ nanofillers, $Cu_2[Mo(CN)_8]\cdot 8H_2O$(CuMo), $RbMn[Fe(CN)_6]$ (RbMnFe), $Co_3[W(CN)_8]_2\cdot$(pyrimidine)$_4\cdot 6H_2O$ (CoW), $Fe_2[Nb(CN)_8]\cdot$(4-pyridinealdoxime)$_8\cdot 2H_2O$ (FeNb), and liquid crystal polymers embedded with spinel ferrites (Mn, Zn, Fe)$_3O_4$ or Spiropyran-protected FePt nanoparticles. The thickness of smart polymer layer 522 can be between 500 nm and 10 microns.

In operation 5L, handling wafer 518 can be removed. In some embodiments, wax layer 516 can be melted to separate handling wafer 518 from Si substrate 502. The resulting probe structure can include Si substrate 502; dielectric layer 504; metallic layers 506, 508, and 510; biocompatible insulation layer 514; and smart polymer layer 522. Note that, because smart polymer layer 522 also has superior biocompatibility, it can be the top layer of the implantable probe, direct contacting biological matter (e.g., the human brain).

Figure 6A:
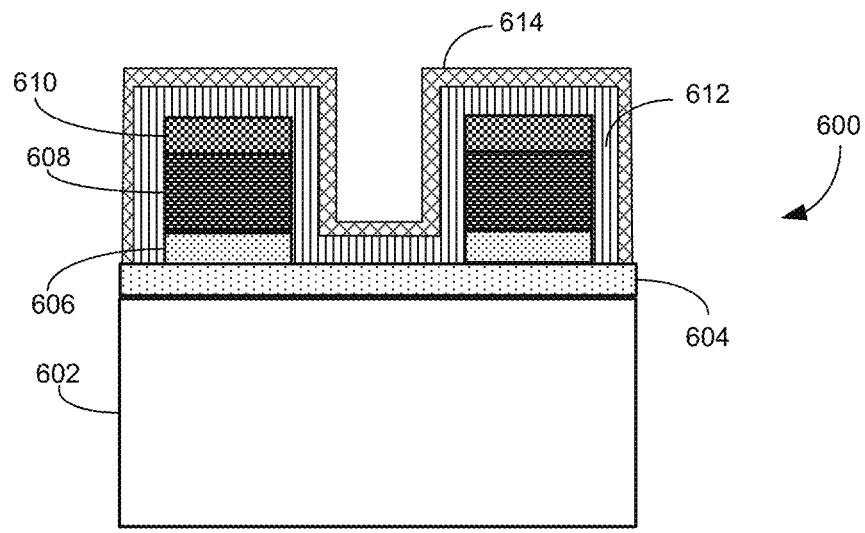
FIG. 6A illustrates the cross-section of an exemplary implantable biomedical probe, according to one embodiment.

Other fabrication processes can also be possible. In some embodiments, instead of spin-coating the smart polymer layer after the DRIE operation that defines boundaries of the probe structures, the smart polymer layer can be deposited on the metal layers before the deposition of the biocompatible insulation layer. This way, the smart polymer layer can be situated between the biocompatible insulation layer and the metal layers. FIG. 6A illustrates the cross-section of an exemplary implantable biomedical probe, according to one embodiment.

Implantable biomedical probe 600 can include a Si substrate 602, and an insulation layer 604 positioned above Si substrate 602. In some embodiments, insulation layer 604 can include a thin layer (e.g., 150 nm) of $SiO_2$. A patterned stack of metallic layers (e.g., metallic layers 606, 608, and 610) can be formed on top of insulation layer 604. The metallic layers are patterned based on the designed locations of the metal coil or coils, connection paths, and metal fingers. In some embodiments, metallic layer 606 can include a thin layer (e.g., 20 nm) of Mo—Cr alloy, metallic layer 608 can include an Au layer having a thickness of around 2 microns, and metallic layer 610 can include a thin layer (e.g., 3 nm) of Ti—W. In further embodiments, the metal coil formed by metallic layers 606, 608, and 610 can have a width of around 10 microns.

A smart polymer layer 612 can be positioned above and completely cover metallic layers 606, 608, and 610. Smart polymer layer 612 can include but is not limited to: liquid crystal polymers with anisotropic $Fe_2O_3$ nanofillers, $Cu_2[Mo(CN)_8]\cdot 8H_2O$(CuMo), $RbMn[Fe(CN)_6]$ (RbMnFe), $Co_3[W(CN)_8]_2\cdot$(pyrimidine)$_4\cdot 6H_2O$ (CoW), $Fe_2[Nb(CN)_8]\cdot$(4-pyridinealdoxime)$_8\cdot 2H_2O$ (FeNb), and liquid crystal polymers embedded with spinel ferrites (Mn, Zn, Fe)$_3O_4$ or Spiropyran-protected FePt nanoparticles. Smart polymer layer 612 can be sufficiently thick to ensure adequate photomagnetic effect. The thickness of smart polymer layer 612 can be between 500 nm and 1 micron.

Implantable probe 600 can also include a biocompatible insulation layer 614 covering smart polymer layer 612. Biocompatible insulation layer 614 can be transparent to allow external light to shine on smart polymer layer 612. In some embodiments, biocompatible insulation layer 614 can include $SiON_x$, and the thickness of $SiON_x$ layer 614 can be around 500 nm.

In some embodiments, a similar spin-coating technique can be used to deposit smart polymer layer 612 onto the metal layers after patterning of the metal layers. As a result, smart polymer layer 612 can cover all surfaces of the metal stack. In some embodiments, smart polymer layer 612 can also be patterned. In other words, smart polymer layer 612 only covers certain regions of the metal stack surface. For example, if one can predetermine regions on the coil that may need light excitation, only those regions can be covered by smart polymer layer 612. In such a scenario, a photolithography process can be performed to deposit a patterned smart polymer layer.

Figure 6B:
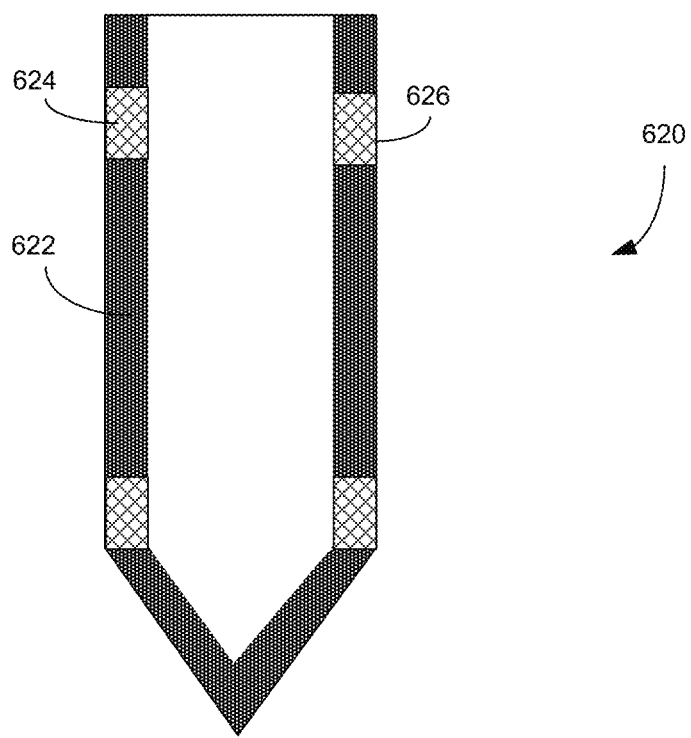
FIG. 6B shows a partial top view of an exemplary implantable probe, according to one embodiment.

FIG. 6B shows a partial top view of an exemplary implantable probe, according to one embodiment. Implantable probe 620 can include a metallic coil 622, which can generate an EM field when excited by AC current. In the example shown in FIG. 6B, metallic coil 622 is positioned along the edges of the top surface of implantable probe 620. FIG. 6B also shows that portions of the top surface of metallic coil 622 can be covered by a layer of smart polymer. For example, portions 624 and 626 of metallic coil 622 are covered by a layer of smart polymer. Due to the photomagnetic property of the smart polymer, when light shines onto a particular spot in the smart polymer region, the local magnetic susceptibility changes abruptly, thus resulting in changes in the excited EM field. More specifically, the peak locations of the E-field gradient can shift due to the effect of the light.

Operating Implantable Probes

Figure 7:
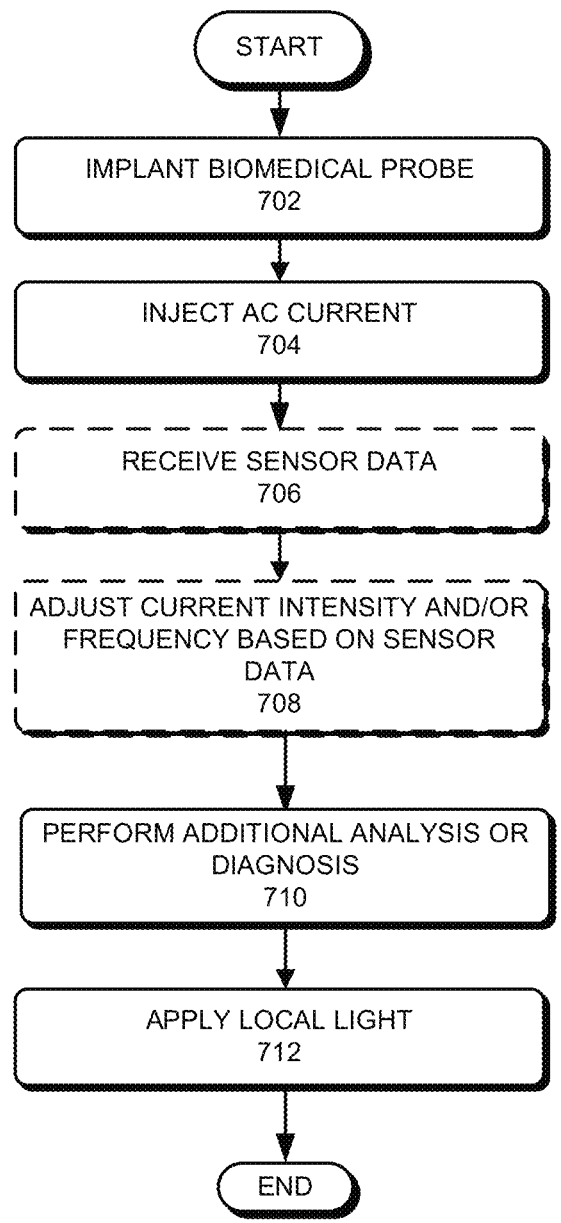
FIG. 7 presents a flowchart illustrating an exemplary process of controlling an electromagnetic field generated by an implantable biomedical probe, according to one embodiment.

FIG. 7 presents a flowchart illustrating an exemplary process of controlling an electromagnetic field generated by an implantable biomedical probe, according to one embodiment. During operation, an implantable probe can be inserted into biological matter (e.g., a human brain) (operation 702). AC current can be injected into one or more metal coils on the implantable probe, exciting an EM field in regions surrounding the probe (operation 704). In some embodiments, the intensity of the AC current can be between 1 and 60 mA (e.g., about 10 mA), and the frequency of the AC current can be between 1 and 5 kHz (e.g., about 3 kHz). The depth of the region within the biological matter that can be affected by the excited EM field can be in the range between 50 and 150 microns.

In some embodiments, the system may optionally receive sensor data from the implantable probe (operation 706) and adjust the intensity and/or frequency of the AC current based on received sensor data (operation 708). Additional analysis or diagnosis may also be performed to determine if a different location within the biological matter needs E-field gradient stimulation (operation 710). For example, cognitive analysis of a person with a probe implanted inside his brain may indicate that a different location near the probe needs stimulation. Alternatively, the E-field gradient location may need to be shifted according to a predetermined path (e.g., according to a predetermined treatment plan).

If it is determined that the EM field needs to be modulated such that the E-field gradient can shift its location, light can be applied externally at a particular spot in order to move the peaks of the E-field gradient (operation 712). In some embodiments, a laser can be used to shine light, from outside of the biological matter, onto the probe implanted within the biological matter. In order to penetrate the biological matter (e.g., a human brain), the laser can have a wavelength between 700 and 1200 nm, preferably between 900 and 1000 nm. Because the metal coil generating the EM field can be covered by a smart polymer layer that changes its magnetic susceptibility under the influence of the light, applying localized light (e.g., using a laser beam) can change the local magnetic susceptibility of the probe, thus changing the surrounding EM field. The spot size of the laser beam can be around a few hundred nanometers. Note that removal of the light will cause the local magnetic susceptibility to return to its original value.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules or apparatus. The hardware modules or apparatus can include, but are not limited to, application-specific integrated circuit (ASIC) chips, field-programmable gate arrays (FPGAs), dedicated or shared processors that execute a particular software module or a piece of code at a particular time, and other programmable-logic devices now known or later developed. When the hardware modules or apparatus are activated, they perform the methods and processes included within them.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. An implantable biomedical probe for generating an electromagnetic field, comprising:
   a substrate;
   one or more metallic coils positioned above the substrate, wherein at least one metallic coil is coupled to an alternating current (AC) current source, and wherein the one or more metallic coils are configured to generate the electromagnetic field surrounding the implantable biomedical probe; and
   a smart polymer layer positioned above the one or more metallic coils, wherein the smart polymer layer comprises at least one photo-switching magnetic material that changes magnetic susceptibility in response to optical stimuli, thereby facilitating adjustment of the electromagnetic field surrounding the implantable biomedical probe by applying the optical stimuli.

2. The implantable biomedical probe of claim 1, wherein the substrate comprises Si, and wherein the substrate's thickness is between 100 and 300 nm.

3. The implantable biomedical probe of claim 1, wherein the one or more metallic coils are coplanar, and wherein a metallic coil is positioned around edges of the substrate.

4. The implantable biomedical probe of claim 1, further comprising a first insulation layer positioned between the substrate and the one or more metallic coils.

5. The implantable biomedical probe of claim 4, wherein the first insulation layer comprises $SiO_2$.

6. The implantable biomedical probe of claim 4, wherein a thickness of the first insulation layer is between 100 and 200 nm.

7. The implantable biomedical probe of claim 1, further comprising a second insulation layer positioned above the one or more metallic coils.

8. The implantable biomedical probe of claim 7, wherein the second insulation layer comprises $SiNO_x$.

9. The implantable biomedical probe of claim 7, wherein the second insulation layer has a thickness between 100 nm and 1 micron.

10. The implantable biomedical probe of claim 7, wherein the smart polymer layer is positioned between the one or more metallic coils and the second insulation layer.

11. The implantable biomedical probe of claim 7, wherein the smart polymer layer is positioned above the second insulation layer.

12. The implantable biomedical probe of claim 1, wherein the at least one metallic coil comprises an Au layer.

13. The implantable biomedical probe of claim 12, wherein the Au layer has a thickness between 1 and 10 microns and a width between 5 and 30 microns.

14. The implantable biomedical probe of claim 12, wherein the at least one metallic coil further comprises:
   a Ti—W layer positioned above the Au layer, wherein the Ti—W layer has a thickness between 1 and 10 nm; and
   a Mo—Cr layer positioned between the substrate and the Au layer, wherein the Mo—Cr layer has a thickness between 10 and 50 nm.

15. The implantable biomedical probe of claim 1, wherein the smart polymer layer comprises one or more of:
   liquid crystal polymers with anisotropic $Fe_2O_3$ nanofillers;
   $Cu_2[Mo(CN)_8] \cdot 8H_2O$ (CuMo);
   $RbMn[Fe(CN)_6]$ (RbMnFe);
   $Co_3[W(CN)_8]_2 \cdot (pyrimidine)_4 \cdot 6H_2O$ (CoW);
   $Fe_2[Nb(CN)_8] \cdot (4\text{-pyridinealdoxime})_8 \cdot 2H_2O$ (FeNb);
   liquid crystal polymers embedded with spinel ferrites (Mn, Zn, Fe)$_3O_4$; and
   liquid crystal polymers embedded with Spiropyran-protected FePt nanoparticles.

16. A biomedical system, the system comprising:
   an implantable probe for generating an electromagnetic field, which comprises:
   a substrate;
   one or more metallic coils positioned above the substrate, wherein at least one metallic coil is configured to be coupled to an alternating current (AC) current source, and wherein the one or more metallic coils are configured to generate the electromagnetic field surrounding the implantable biomedical probe; and
   a smart polymer layer positioned above the metallic coils, wherein the smart polymer layer comprises at least one photo-switching magnetic material that changes magnetic susceptibility in response to optical stimuli, thereby facilitating adjustment of the electromagnetic field surrounding the implantable biomedical probe by applying the optical stimuli;

a probe connector electrically coupled to the implantable probe, wherein the probe connector comprises a plurality of metallic fingers; and a printed circuit board, which comprises a cable connector and an input/output port electrically coupled to each other, wherein the cable connector is electrically coupled to metallic fingers of the probe connector via a flexible cable, and wherein the input/output port is configured to be electrically coupled to an external power-and-control unit for providing power.

17. The biomedical system of claim 16, wherein the smart polymer layer comprises one or more of:

liquid crystal polymers with anisotropic $Fe_2O_3$ nanofillers;

$Cu_2[Mo(CN)_8].8H_2O(CuMo)$;

$RbMn[Fe(CN)_6]$ (RbMnFe);

$Co_3[W(CN)_8]_2.(pyrimidine)_4.6H_2O$ (CoW);

$Fe_2[Nb(CN)_8].(4\text{-pyridinealdoxime})_8.2H_2O$ (FeNb);

liquid crystal polymers embedded with spinel ferrites $(Mn, Zn, Fe)_3O_4$; and liquid crystal polymers embedded with Spiropyran-protected FePt nanoparticles.

18. A method for fabricating an implantable biomedical probe, the method comprising:

preparing a Si substrate;

forming one or more metallic coils positioned above the Si substrate, wherein at least one metallic coil is configured to be coupled to an alternating current (AC) current source and wherein the one or more metallic coils are configured to generate the electromagnetic field surrounding the implantable biomedical probe; and depositing a smart polymer layer above the one or more metallic coils, wherein the smart polymer layer comprises at least one photo-switching magnetic material that changes magnetic susceptibility in response to light, thereby facilitating adjustment of the electromagnetic field surrounding the implantable biomedical probe by applying the optical stimuli.

19. The method of claim 18, wherein the smart polymer layer comprises one or more of:

liquid crystal polymers with anisotropic $Fe_2O_3$ nanofillers;

$Cu_2[Mo(CN)_8].8H_2O(CuMo)$;

$RbMn[Fe(CN)_6]$ (RbMnFe);

$Co_3[W(CN)_8]_2.(pyrimidine)_4.6H_2O$ (CoW);

$Fe_2[Nb(CN)_8].(4\text{-pyridinealdoxime})_8.2H_2O$ (FeNb);

liquid crystal polymers embedded with spinel ferrites $(Mn, Zn, Fe)_3O_4$; and liquid crystal polymers embedded with Spiropyran-protected FePt nanoparticles.

20. The method of claim 18, wherein the at least one metallic coil comprises an Au layer having a thickness between 1 and 10 microns and a width between 5 and 30 microns.

* * * * *